(12) United States Patent
Velthuis et al.

(10) Patent No.: US 9,517,358 B2
(45) Date of Patent: Dec. 13, 2016

(54) UPSTREAM DIRECT X-RAY DETECTION

(75) Inventors: Jaap Velthuis, Bristol (GB); Peter Richard Hugtenburg, Swansea (GB); Catherine Hall, Bristol (GB); Ryan Page, Bristol (GB); Paul Stevens, Bristol (GB)

(73) Assignee: THE UNIVERSITY OF BRISTOL, Bristol (GB)

( * ) Notice: Subject to any disclaimer, the term of this patent is extended or adjusted under 35 U.S.C. 154(b) by 461 days.

(21) Appl. No.: 13/996,616

(22) PCT Filed: Dec. 21, 2011

(86) PCT No.: PCT/GB2011/001747
§ 371 (c)(1),
(2), (4) Date: Sep. 9, 2013

(87) PCT Pub. No.: WO2012/085507
PCT Pub. Date: Jun. 28, 2012

(65) Prior Publication Data
US 2014/0010352 A1 Jan. 9, 2014

(30) Foreign Application Priority Data

Dec. 22, 2010 (GB) .................................. 1021841.0

(51) Int. Cl.
*G01T 1/02* (2006.01)
*A61N 5/10* (2006.01)
*G01T 1/24* (2006.01)

(52) U.S. Cl.
CPC ........... *A61N 5/1071* (2013.01); *A61N 5/1065* (2013.01); *G01T 1/24* (2013.01); *A61N 5/1047* (2013.01); *A61N 5/1075* (2013.01)

(58) Field of Classification Search
CPC ....................................................... A61N 5/10
See application file for complete search history.

(56) References Cited

U.S. PATENT DOCUMENTS

| | | | |
|---|---|---|---|
| 6,038,284 A * | 3/2000 | Hernandez-Guerra et al. | 378/65 |
| 7,582,875 B2 * | 9/2009 | Caccia et al. | 250/370.07 |
| 7,851,764 B2 * | 12/2010 | Jin | H01J 37/244 250/370.08 |

* cited by examiner

*Primary Examiner* — David J Makiya
*Assistant Examiner* — Dani Fox
(74) *Attorney, Agent, or Firm* — Huffman Law Group, PC (57) ABSTRACT

A radiation beam, for example a therapeutic radiation beam such as an IMRT or VMAT X-ray beam is monitored using a Monolithic Active Pixel Sensor (MAPS) detector. Photons of the radiation beam can interact with the MAPS detector, and the radiation beam configuration can be estimated from the determined positions of the interactions. The detector is made sufficiently thin that it interacts only very weakly with the X-ray photons. For example, less than 1 in $10^3$ of the X-ray photons might interact with the detector. Hence, the disturbance to the X-ray beam is negligible.

10 Claims, 10 Drawing Sheets

UPSTREAM DIRECT X-RAY DETECTION

RELATED APPLICATIONS

This application is a national stage application of International patent application no. PCT/GB2011/001747, filed Dec. 21, 2011. This application also claims priority to Great Britain Patent Application No. 1021841.0, filed Dec. 22, 2010.

BACKGROUND AND SUMMARY

Many cancer patients are treated using high energy X-Ray photon irradiation. For some cancers this presents the difficulty that the tumor might be located very close to radiation sensitive body parts. A recent development in ionizing radiation therapy is to produce a strongly position dependant intensity variation within a single beam by combining many intricate beam shapes which can, for example, be created by thin tungsten leaf collimators absorbing discreet regions of an x-ray beam. The leaf motion may either be in discrete steps or continuous. In a technique often called Intensity Modulated Radiation Therapy (IMRT), typically about seven such beams are combined from different static directions by means of a rotating gantry. Alternatively, both the leaf positions, and the beam direction, are continuously updated while the beam is on, a technique often referred to as Volumetric Arc Therapy (VMAT).

Before a patient is treated with such a complicated beam configuration, a pre-treatment measurement needs to be done. In this measurement, essentially, the treatment program is executed and the dose is measured using a water phantom. The need for the pre-treatment measurement doubles the time required to treat a patient.

It would therefore be desirable to measure the radiation dose in the patient during the radiation treatment itself, but this is very difficult. Measuring the dose downstream of the patient is notoriously difficult as the patient acts as a very complicated scattering centre.

U.S. Pat. No. 6,853,702 discloses a radiation dosimetry system, in which an imaging device is placed between the radiation source and the patient, and is used to form an image of the radiation field. EP-2108328-A discloses another system, in which a detector device, formed from an array of ionization chambers, is positioned between the multileaf collimator and the patient, and is used to determine the radiation dose delivered to the patient. Several millimeters of a water-equivalent material is typically placed upstream of the detector volume, in order for sufficient photons to interact with the detector to distinguish the therapeutic component of the beam from contaminant components such as electrons, which have differing radiation profile, and which only penetrate the skin of the patient.

However, these prior art systems fail to recognize that typically, if one puts a detector upstream of the patient, the beam is disturbed, resulting in photon scattering and the production of secondary electrons, and as a result a different dose in the patient is realized. In the case of a detector having a thickness of several millimeters of water-equivalent material, the beam might be attenuated by several percent, and the out of field intensity might increase by several tens of percent due to scattering.

According to a first aspect of the invention, there is provided a method of monitoring a radiation beam, the method comprising:
 placing in the beam a MAPS detector;
 exposing the MAPS detector to the radiation beam, such that photons of the radiation beam can interact with the MAPS detector;
 determining a position of each identified interaction; and
 estimating the radiation beam configuration from the determined positions of the interactions.

Thus, the detector of the present invention might interact with the radiation beam only 1% as much as the prior art detector. As a result, the disturbance to the beam is much smaller.

BRIEF DESCRIPTION OF THE DRAWINGS

For a better understanding of the present invention, and to show how it can be put into effect, reference will now be made, by way of example only, to the accompanying drawings, in which.

DETAILED DESCRIPTION

Figure 1:
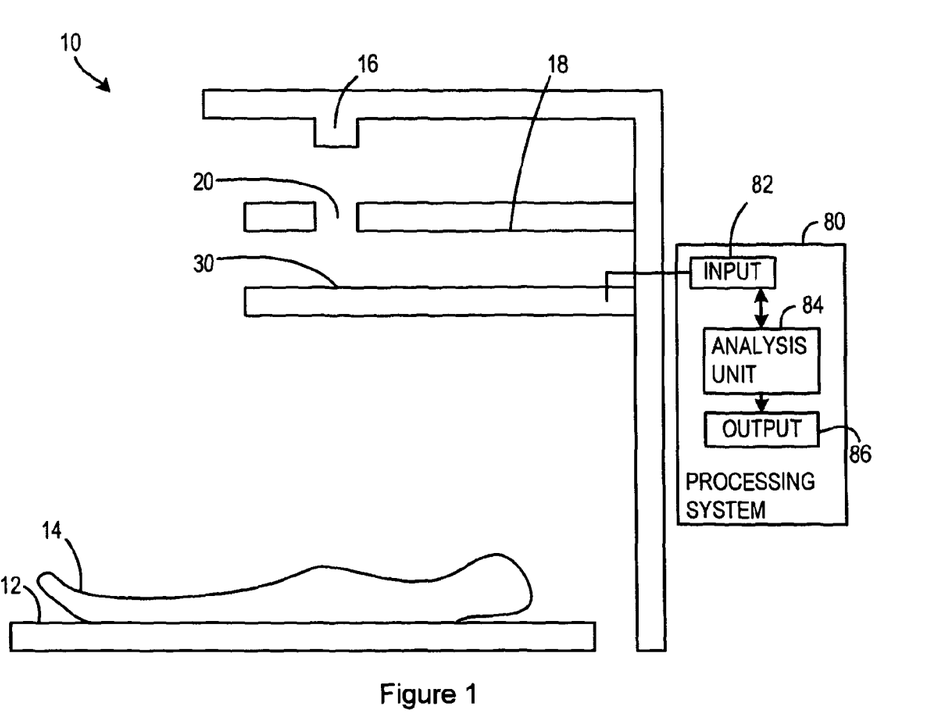
FIG. 1 illustrates a radiation treatment system in accordance with an aspect of the invention.

FIG. 1 is a schematic illustration, showing parts of a radiation treatment system 10 in accordance with an aspect of the invention. It will be understood by the person skilled in the art that FIG. 1 only shows those parts of the system 10 that are relevant for an understanding of the present invention. The system 10 includes a surface 12 on which a patient 14 can be positioned, and a radiation source 16 that is able to direct radiation towards the patient 16. In this embodiment, the radiation source 16 is a source of X-rays.

For example, the radiation source can operate by accelerating electrons in a small linear accelerator. These electrons collide with a target, and this generates bremsstrahlung X-rays. These X-rays have a varying energy. In addition, secondary electrons are generated. This results in a beam consisting of electrons and X-rays, although the dose to the tumour is solely due to X-rays having an interaction inside the body of the patient 14.

Located between the radiation source 16 and the patient 14 is a multi-leaf collimator 18, which defines an opening 20 through which the radiation can pass.

Figure 2:
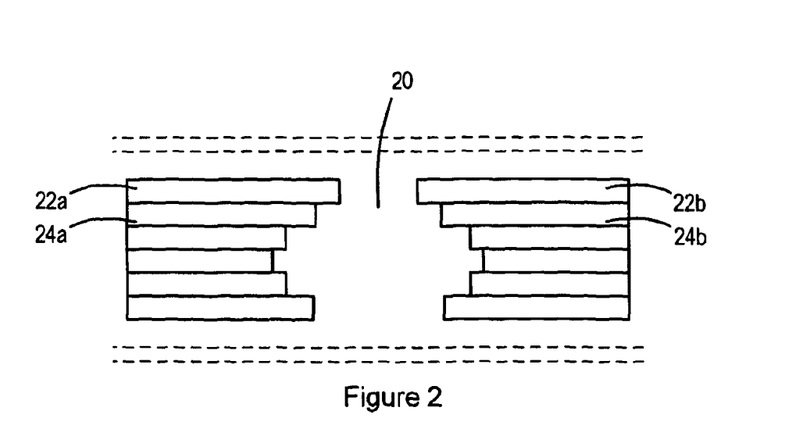
FIG. 2 illustrates a multileaf collimator in the system of FIG. 1.

As shown in plan view in FIG. 2, the collimator 18 includes multiple leaves 22a, 22b; 24a, 24b, etc. The leaves are made of a material, such as tungsten, which is opaque to the radiation. The leaves of each pair can be moved towards or away from each other, in order to define an opening 20 through which the radiation can pass.

Controlling the size and shape of the opening 20 therefore produces a radiation beam of a highly controllable shape.

This allows the radiation dose supplied to the patient to be controlled, using an Intensity Modulated Radiation Therapy (IMRT) technique.

The gantry containing the radiation source 16 can be rotated about an axis that might for example lie in the plane of the Figure, and in the plane of the patient support surface 12. In this case, both the leaf positions, and the beam direction, are continuously updated while the beam is on, in a technique known as Volumetric Arc Therapy (VMAT).

Located between the collimator 18 and the patient 14 is an upstream X-ray radiation detector 30. As an example, the distance between the sensor 30 and the collimator opening 20 can be about 10 cm. Specifically, the detector 30 takes the form of a large area, radiation hard, Monolithic Active Pixel Sensor. More specifically, in one embodiment, the detector 30 is a known device, known as a Vanilla sensor. The Vanilla is a monolithic active pixel sensor designed in 0.35 μm CMOS technology. It has 520×520 pixels that are 25×25 μm$^2$ in size. It can be read out either in digital or in analogue mode. In digital mode, the digitisation is done on chip, and the maximum frame rate is 150 frames per second. In analogue mode, an external ADC is used.

In another embodiment, the detector 30 can be an Achilles sensor, which has 16 M pixels, a 14 μm thick epilayer, and 14×14 μm$^2$ pixels. It has a maximum frame rate of 40 frames per second when reading out full frames, but the sensor also has "region of interest read out", which means that one can select an area to be read out, and this then goes faster. For example, it is possible firstly to quickly verify the positions of the leaves that just have been moved and then measure the dose rate at various locations. This can be used to optimize the verification procedure. Also, it can be foreseen that one area of the beam profile is particularly dangerous. Hence, it can be advantageous to monitor this area of the beam very precisely, while other parts might need to be checked only occasionally.

The detector 30 is connected to a processing system 80, which includes an input 82, for receiving electronic signals generated by the detector 30, an analysis unit 84, and an output 86, for providing results to a user of the system, for example visually, either in real time or after the event, or by means of an audible alarm in the event that the detected beam is not as intended. The analysis unit is able to detect a signal level for each pixel of the detector in each frame period, and then determine which of these pixel levels represent interactions with photons, and then generate an output that indicates a configuration of the X-ray beam based on the pattern of pixels in which there have been a certain number of hits over a particular time period.

The analysis unit 84 can take the form of a suitably programmed computer.

Figure 3:
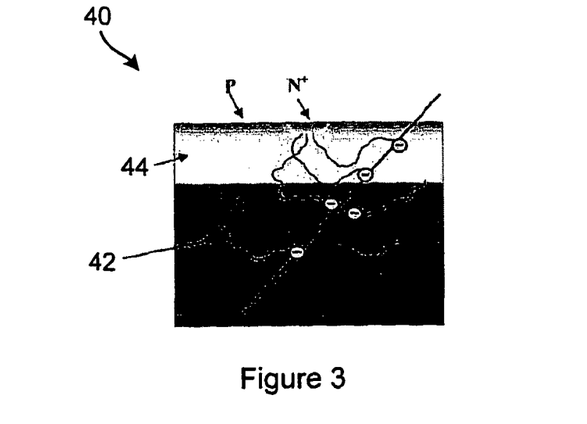
FIG. 3 is a schematic cross-sectional view through a Monolithic Active Pixel Sensor.

FIG. 3 is a schematic cross-section through a typical MAPS device 40, provided purely for the purposes of illustration. The MAPS device 40 consists of a sandwich structure including a highly doped (p++) substrate 42 which typically has a thickness in the region of 300-500 μm. On the substrate is grown a layer 44 of lowly doped p-type material. This layer is known as the epitaxial layer, and the required electronic circuitry is formed on this.

Occasionally, an X-ray photon or contamination electron interacts with the epitaxial layer of the sensor. This process may result in the production of electron-hole pairs. Some of these electrons will perform a random walk through the epitaxial layer 44, while being unable to escape the epitaxial layer due to the built-in potential difference between the substrate and the epitaxial layer material due to the different doping concentrations. If such an electron gets close enough to a collection diode, the charge is removed from the epilayer and read out. Pixel sizes typically range from about 5 μm to 50 μm.

The thickness of the epilayer is set by the technology process in which the device is designed. It will typically be in the range from a few microns up to 30 μm.

The substrate is mainly required for mechanical support. It requires a thickness of only a few microns to form the necessary potential barrier to lock in the electrons. The rest can be removed without penalty to the performance. In some embodiments of the invention, the sensor is made as thin as possible, typically 25 to 50 micron but more preferably 30-40 micron thick, and it is mounted on a very low mass mechanical substrate, such as a 3% relative density carbon foam.

The MAPS device can have a thickness in the region of only 30 μm without losing signal. Fewer than 1 in 10$^3$ X-ray photons, and typically only 1 in 10$^5$ X-ray photons, will convert in the sensitive layer and produce a signal. The rest of the X-ray beam will leave the sensor undisturbed. This means that the presence of the detector 30 has a negligible effect on the radiation dose reaching the patient 14.

As mentioned above, in order to improve the mechanical stability of the sensor, it is mounted on a very low mass mechanical substrate, such as a 3% relative density carbon foam. This will also not disturb the beam. Thus, the detector system can be placed upstream of the patient without disturbing the energy deposited in the patient.

Figure 4:
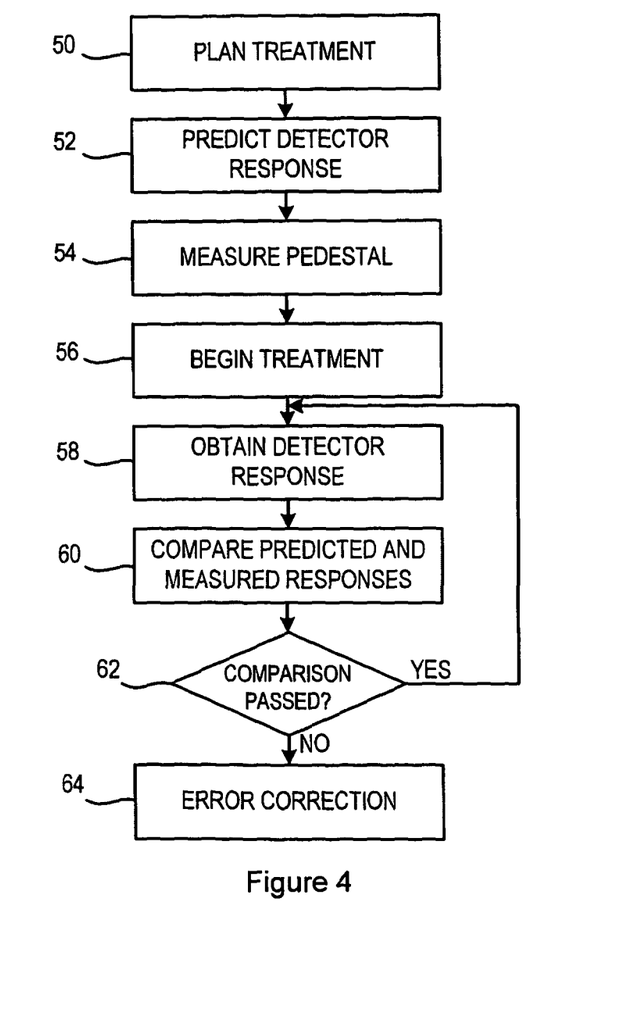
FIG. 4 is a flow chart, illustrating methods in accordance with aspects of the invention.

FIG. 4 is a flow chart, illustrating aspects of a method in accordance with the invention.

In step 50, an Intensity Modulated Radiation Therapy (IMRT) treatment plan is determined. This will for example require a specific dose of radiation to be delivered to the patient 14 in a specific pattern. The intensity of the dose and/or the beam shape might vary over time. In step 52, the response of the MAPS detector 30 is predicted, assuming that the intended dose is being delivered to the patient. If the planned intensity of the dose and/or the beam shape vary over time, the predicted response of the MAPS detector 30 will similarly vary over time.

Every pixel of the sensor 30 has its own dark signal level, the pedestal. In step 54, the pedestal is measured with the beam off. This step might be performed once during each treatment as shown in FIG. 4, or might be performed much less often. In the later analysis, the signals are corrected for the pedestal.

In step 56, the treatment is started and, in step 58, the MAPS detector response is obtained. In step 60, the obtained detector response is compared with the predicted MAPS detector response at that time. Assuming that the comparison is successful, the process returns to step 58, and continues.

However, if the comparison in step 62 indicates that the difference between the obtained detector response and the predicted detector response at that time exceeds a threshold, the process passes to step 64, and a correction step is performed.

The correction step 64 might comprise signalling to an operator that an error has occurred and/or automatically stopping the treatment. As an alternative, if the comparison identifies that the beam shape does not match the intended beam shape, the collimator positions can be adjusted as required.

As the generated charge in the sensor is directly depending on the X-ray photon flux, one can monitor the local dose in the patient in real-time. Therefore, it is no longer necessary to do the pre-treatment measurements. The Monolithic Active Pixel Sensors (MAPS) can measure the beam very quickly, and precisely, and so this allows fast monitoring of the beams and hence timely intervention during possible mistreatment in IMRT, for example giving an alarm within a second to turn off the linac or adjust the tungsten finger positions.

Aspects of the invention are therefore concerned with the use of a MAPS based system for an upstream fast, 2-dimensional, position dependent intensity measurement of radiation beams, for example during IMRT.

The measurement of the beam will now be described, by way of an illustrative example, in which the radiation source 16 produces a 6 MV beam, containing X-rays of various energies, such as to produce a patient dose of around 350 MU/min.

Figure 5A:
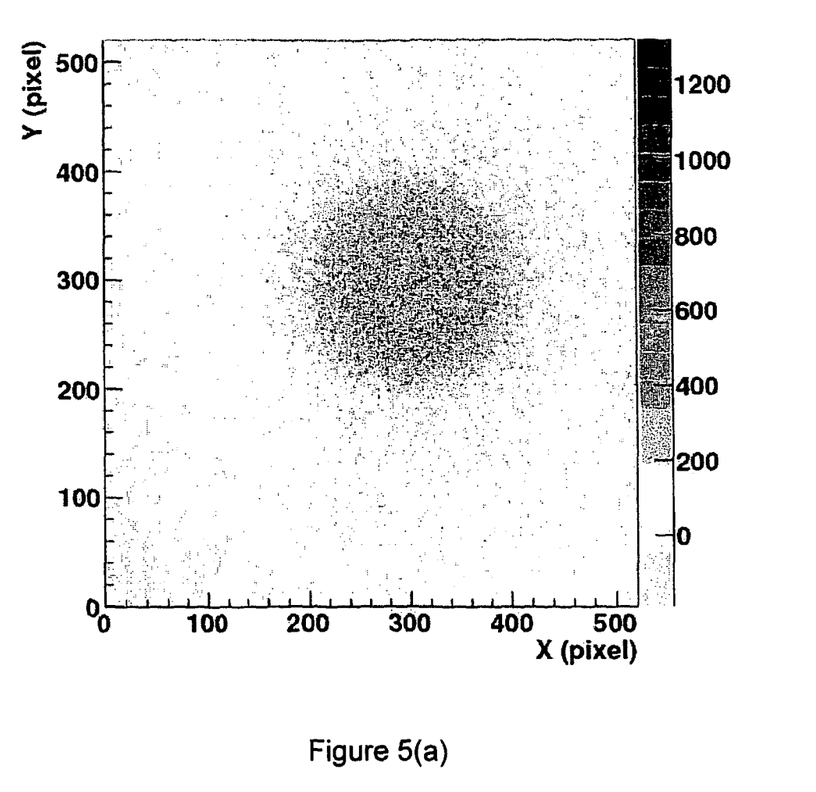
FIG. 5 shows a signal level obtained from the detector of the present invention as a function of position in a horizontal X-Y plane at different frame rates.
Figure 5B:
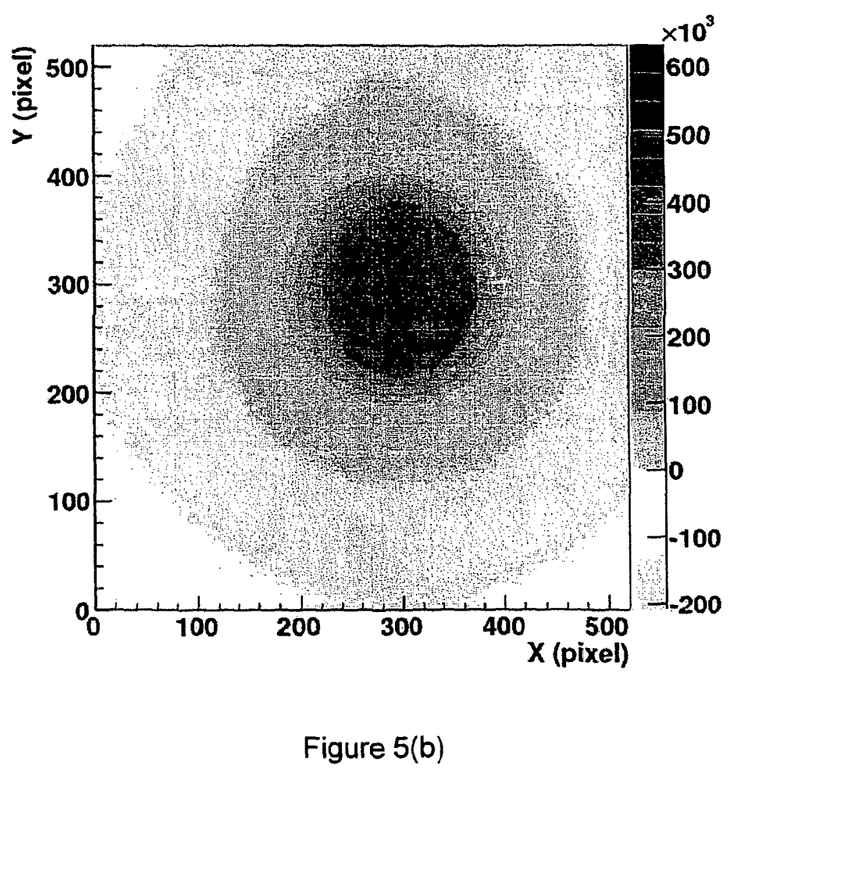
Figure 6A:
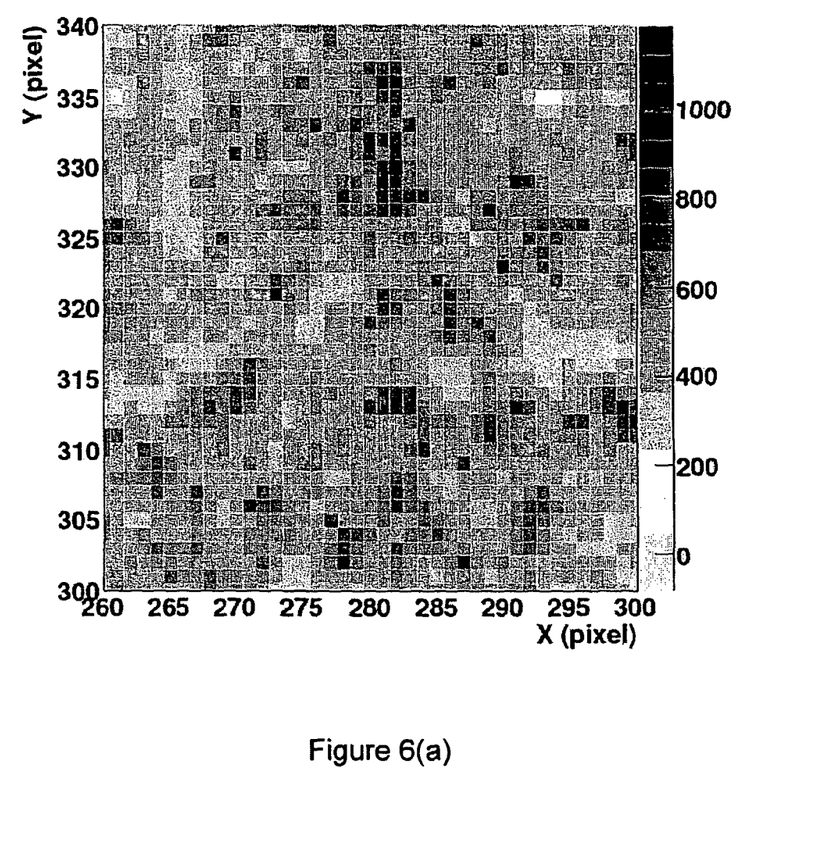
FIG. 6 shows the signal level as a function of position in a small part of interest of the horizontal X-Y plane where the beam is most intense, at different frame rates.
Figure 6B:
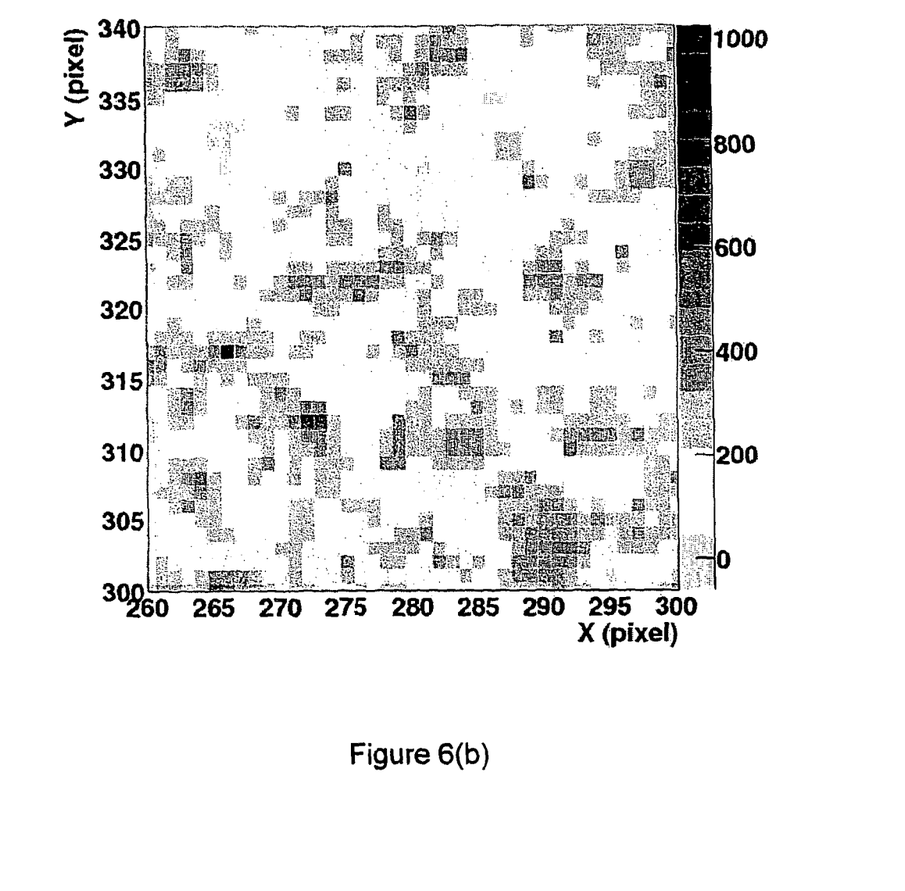
Figure 6C:
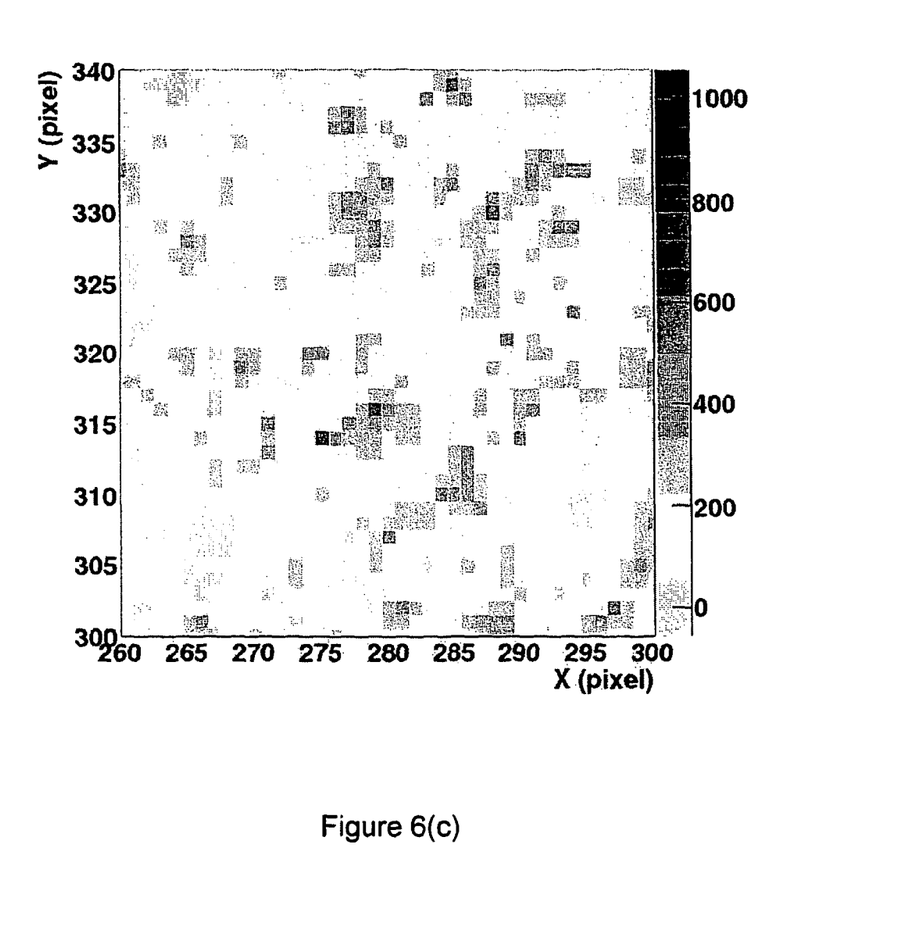
Figure 6D:
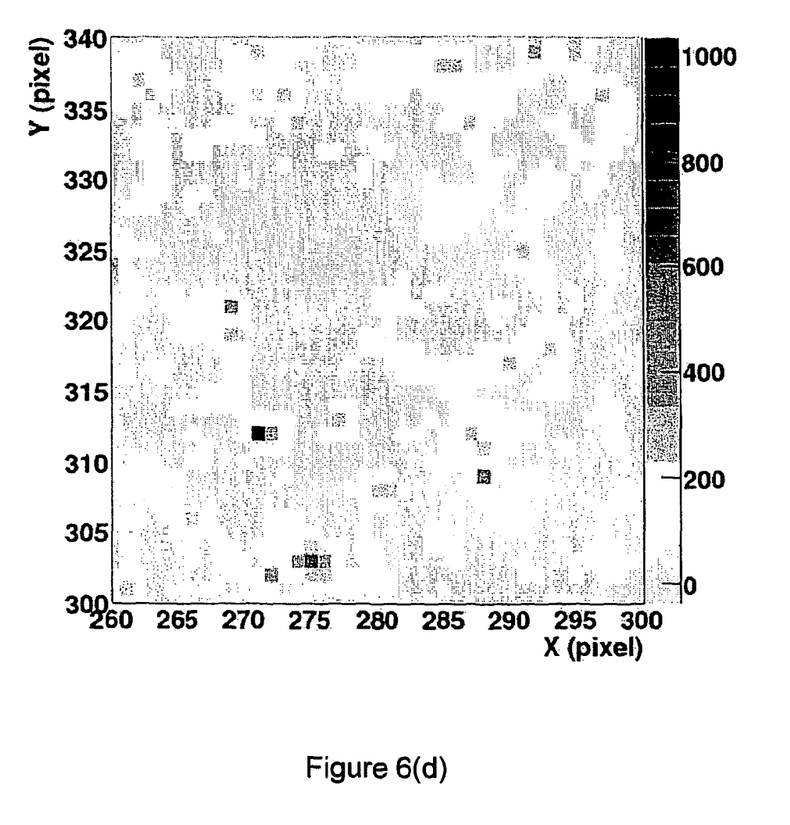

FIG. 5(*a*) shows the signal level, corrected for the pedestal, as a function of position in a horizontal X-Y plane for a typical frame, using analogue read out at 8 frames per second, while the beam has a nominal treatment strength of 400 MU/min and a beam repetition rate of about 100 Hz. Hence, FIG. 5(*a*) represents the result of integrating over 12 pulses of the beam. One can clearly see the beam and also notice that pixels outside of the beam area generally do not have a signal. FIG. 5(*b*) shows this integrated over 1000 frames (i.e. about 12000 linac pulses), which demonstrates that there are some X-rays arriving outside of the collimator area, as could be expected when X-rays scatter inside the collimator.

As mentioned above, when a photon interacts in the epitaxial layer, electron-hole pairs will be produced. The electrons are diffusing inside the epitaxial layer until they reach an electrode and are collected. FIG. 6 shows the signal level as a function of position in a small part of interest of the horizontal X-Y plane where the beam is most intense, at different frame rates using the digital read out. Specifically, FIG. 6(*a*) shows the result at 8 frames per second, FIG. 6(*b*) shows the result at 30 frames per second, FIG. 6(*c*) shows the result at 50 frames per second, and FIG. 6(*d*) shows the result at 100 frames per second.

When the flux of photons over the duration of a frame is low enough, i.e. when the frame rate is high enough, i.e. the signal clusters are sufficiently distinct and hence not overlapping too much, individual clusters can be reconstructed. In that case, the hit position can be reconstructed with high precision by using reconstruction algorithms based on how the charge is shared. Also the number of photons can be counted with high precision. Specifically, when reading out the sensor at ~40 frames per second, individual clusters can be reconstructed and hence the position variation in the intensity of the beam can be measured very precisely.

Moreover, this allows one to distinguish between events resulting from the interaction of a photon with the sensor, and events resulting from the interaction of an electron with the sensor.

More specifically, most background electrons will enter the sensor perpendicular to the plane thereof, within +/−15 degrees. These electrons will deposit some energy and generate a signal according to a Landau distribution. This signal is only spread over 3-4 pixels that are located in a 2×2 area.

X-ray photons that interact with the sensor will often generate a Compton electron, having a relatively high kinetic energy. They start travelling through the epitaxial layer in one direction and generate electron-hole pairs along the way. So, the detector output for such a Compton electron will typically have a comet-like shape. The typical track length is larger than the pixels in the detector, and provided that it extends over two or more pixels, this allows the track to be distinguished from that of background electrons.

Thus, when a pixel with a high signal is detected, the surrounding 8 pixels can be examined, to see if there is signal there, followed by the next surrounding ring of 16 pixels. If a signal is found on some of the pixels there, the neighboring pixels on the outside of that ring can be examined. So, this process will find a comet-like tail that is at least 2 pixels long.

Thus, any event can be checked, to determine whether there is a tail, and hence whether it is due to a photon or an electron. The energy dependence of the cross-section for Compton scattering can also be used to ensure only high energy photons are considered.

By examining the clusters, it is therefore possible to select clusters originating predominantly from X-rays, and thereby produce a more accurate estimate of the radiation dose reaching the patient.

Figure 7A:
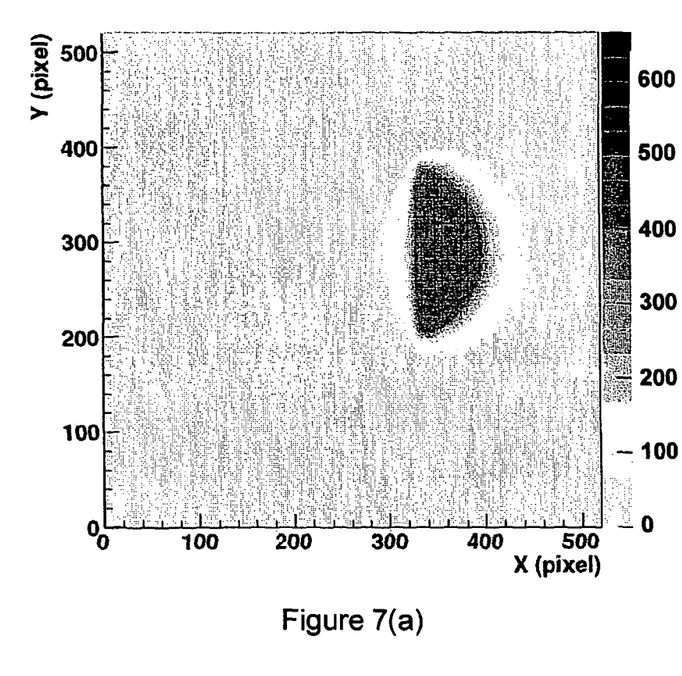
FIG. 7(a) shows a detector output, as a function of position in a horizontal X-Y plane, in a specific test.

In an illustrative example, the beam position was estimated by covering half of the sensor. The data was taken at 8 frames per second. When a pixel signal exceeds a threshold value, it is considered to be hit. Events resulting from the interaction of an electron with the sensor typically produce a lower signal, and so the threshold value can be set so that such events are not counted as a hit, and only events resulting from the interaction of an X-ray photon with the sensor are counted as a hit. Then the number of hits per pixel is counted.

FIG. 7(*a*) shows the number of hits, as a function of position in a horizontal X-Y plane, using an intermediate value (200 ADC counts) for the threshold. Clearly, half the beam is stopped.

To understand how well the beam is stopped, the distribution along the line Y=300 is studied. In an ideal case, the signal drop obeys a block function. However, this is broadened, due to detector uncertainty and, mainly, due to background electrons that scatter and arrive at the detector at larger angles. The signal drop can therefore be modelled by a constant value, that then drops steeply as $e^{-x}$. The drop can alternatively be modelled by a Gaussian distribution, which can be described by the complementary error function $$\mathrm{erfc}(x) = \frac{2}{\sqrt{\pi}} \int_x^\infty e^{-t^2} dt$$

Figure 7B:
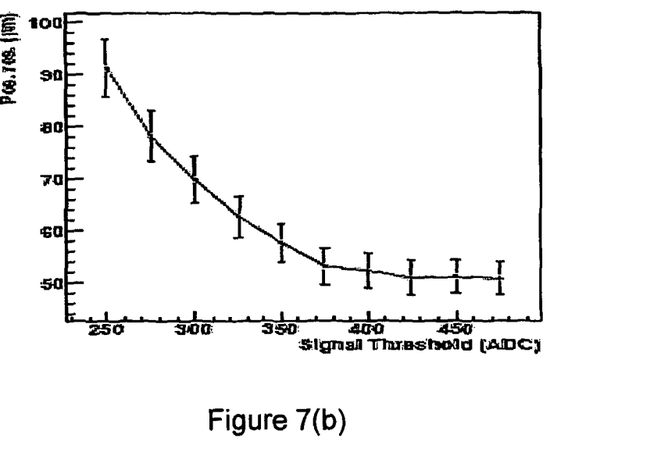
FIG. 7(b) shows the position resolution as a function of a threshold value used in judging the detector output.

Fitting this function and extracting the resolution from the fit for various threshold function demonstrates that best the position resolution obtained with this sensor is 51±3 μm. FIG. 7(*b*) shows the extracted position resolution as a function of the threshold value.

Thus, there is disclosed a monolithic active pixel sensor that can be used as a beam monitor in a therapeutic beam of ionizing radiation, such as an X-ray beam.

The invention claimed is:

1. A method of monitoring an X-ray radiation beam for treatment of a patient, the method comprising:
placing in the radiation beam a monolithic active pixel sensor (MAPS) detector between the patient and an x-ray source;
exposing the MAPS detector to the radiation beam, such that photons of the radiation beam can interact with the MAPS detector wherein the MAPS detector has a thickness configured such that it interacts with a maximum of 1 in $10^3$ photons of the X-ray beam incident on the detector;

determining a position of each identified interaction; and estimating a configuration of the radiation beam delivered to the patient from the determined positions of the interactions.

2. A method as claimed in claim 1, comprising:
exposing the MAPS detector to the radiation beam for a plurality of successive frames; and further comprising:
in each frame, identifying each interaction between a photon of the radiation beam and the MAPS detector;
determining a position of each identified interaction; and estimating the radiation beam configuration from the determined positions of the interactions over the plurality of frames.

3. A method as claimed in claim 1, further comprising:
distinguishing between interactions between incident photons of the radiation beam and the MAPS detector, and interactions between incident electrons and the MAPS detector.

4. A method as claimed in claim 3, comprising:
identifying each interaction between a photon of the radiation beam and the MAPS detector, based on a shape of a cluster of detector pixels excited by the interaction.

5. A method as claimed in claim 4, comprising:
identifying an interaction between a photon of the radiation beam and the MAPS detector, in the event that a cluster of detector pixels excited by the interaction comprises a tail extending linearly over at least three pixels.

6. A radiation detection treatment system, comprising: a radiation source for generating a beam of X-ray radiation; a first surface on which a patient can be positioned and a monolithic active pixel sensor (MAPS) detector, for exposure to a beam of X-ray radiation and configured so as to be located, in use, in the beam of X-ray radiation between the surface and the radiation source, wherein the MAPS detector has a thickness configured such that it interacts with a maximum of 1 in $10^3$ photons of the X-ray beam incident on the detector; and a processing system, wherein the processing system is configured to identify interactions between photons of the radiation beam and the MAPS detector, to determine a position of each identified interaction, and to estimate the radiation beam configuration delivered to the patient from the determined positions of the interactions.

7. A radiation treatment system as claimed in claim 6, wherein the processing system is configured to distinguish between interactions between incident photons of the radiation beam and the MAPS detector, and interactions between incident electrons and the MAPS detector.

8. A radiation treatment system as claimed in claim 7, wherein the processing system is configured to identify each interaction between a photon of the radiation beam and the MAPS detector, based on a shape of a cluster of detector pixels excited by the interaction.

9. A radiation treatment system as claimed in claim 8, wherein the processing system is configured to identify an interaction between a photon of the radiation beam and the MAPS detector, in the event that a cluster of detector pixels excited by the interaction comprises a tail extending linearly over at least three pixels.

10. A method for monitoring and/or signalling errors of a radiation therapy apparatus during delivery of X-ray radiation treatment to a patient, said radiation therapy apparatus being configured for Intensity Modulated Radiation Therapy, the method comprising the steps of: providing a monolithic active pixel sensor (MAPS) between a radiation source and said patient, capable of providing a measured detector response of radiation treatment, wherein the MAPS detector has a thickness configured such that it interacts with a maximum of 1 in $10^3$ photons of the X-ray beam incident on the detector; determining a predicted MAPS detector response for each successive time of the radiation treatment; measuring a MAPS detector response for each successive time of the radiation treatment; performing a comparison between measured MAPS detector response and the corresponding predicted MAPS detector response; and signalling in a short reaction time an error when the comparison results in a difference which exceeds a given threshold.

* * * * *